United States Patent [19]

Miller et al.

[11] 4,055,766
[45] Oct. 25, 1977

[54] CONTROL SYSTEM FOR GAMMA CAMERA

[75] Inventors: Don W. Miller, Westerville; Mark S. Gerber, Columbus, both of Ohio

[73] Assignee: The Ohio State University, Columbus, Ohio

[21] Appl. No.: 680,754

[22] Filed: Apr. 27, 1976

[51] Int. Cl.$^2$ .............................................. G01T 1/22
[52] U.S. Cl. .............................. 250/370; 250/363 S
[58] Field of Search ............................ 250/370, 363 S

[56] References Cited

U.S. PATENT DOCUMENTS

| | | | |
|---|---|---|---|
| 3,812,361 | 5/1974 | Prag et al. | 250/370 |
| 3,984,689 | 10/1976 | Arseneau | 250/363 S |

*Primary Examiner*—Davis L. Willis

*Attorney, Agent, or Firm*—Sidney W. Millard

[57] ABSTRACT

An improved gamma camera arrangement of a variety utilizing a solid state detector, preferably formed of high purity germanium. The central arrangement of the camera operates to effect the carrying out of a trapezoidal filtering operation over antisymmetrically summed spatial signals through gated integration procedures utilizing idealized integrating intervals. By simultaneously carrying out peak energy evaluation of the input signals, a desirable control over pulse pile-up phenomena is achieved. Additionally, through the use of the time derivative of incoming pulse or signal energy information to initially enable the control system, a low level information evaluation is provided serving to enhance the signal processing efficiency of the camera.

29 Claims, 9 Drawing Figures

CONTROL SYSTEM FOR GAMMA CAMERA

The invention described herein was made in the course of work under a grant or award from the Department of Health, Education and Welfare.

BACKGROUND

The field of nuclear medicine has long been concerned with techniques of diagnosis wherein radiopharmaceuticals are introduced into a patient and the resultant distribution or concentration thereof, as evidenced by gamma ray intensities, is observed or tracked by an appropriate system of detection. An important advantage of the diagnostic procedure is that it permits noninvasive investigation of a variety of conditions of medical interest. Approaches of this investigative technique have evolved from early pioneer procedures wherein a hand-held radiation counter was utilized tomap body contained areas of radioactivity to more current systems for simultaneously imaging substantially an entire, in vivo, gamma ray source distribution. In initially introduced practical systems, scanning methods were provided for generating images, such techniques generally utilizing a scintillation-type gamma ray detector equipped with a focusing collimator which moved continuously inselected co-ordinate directions, as in a series of parallel sweeps, to scan regions of interest. A drawback to the scanning technique resides in teh necessarily longer exposure times required for the derivation of an image. For instance, such time elements involved in image development generally are overly lengthy to carry out dynamic studies of organ function.

By comparison to the rectilinear scanner described above, the later developed "gamma camera" is a stationary arrangement wherein an entire region of interest is imaged at once. As initially introduced the stationary camera systems generally utilized a larger diameter sodium Iodide, Na I (TI) crystal as a detector in combination with a matrix of photomultiplier tubes. A multiple channel collimator is interposed intermediate the source containing subject of investigation and this scintillation detector crystal. When a gamma ray emanating from the region of investigative interest interacts with the crystal, a scintillation is produced at the point of gamma ray absorption and appropriate ones of the photomultiplier tubes of the matrix respond to the thus generated light to develop output signals. The original position of gamma ray emanation is determined by position responsive networks associated with the outputs of the matrix. For additional information concerning such camera, see:

I. Anger, H. O., "A New Instrument for Mapping Gamma Ray Emitters", Biology and Medicine Quarterly Report UCRL-3653, 1957.

A continually sought goal in the performance of gamma camera is that of achieving a high resolution quality in any resultant image. Particularly, it is desirable to achieve this resolution in combination with concomitant utilization of a highly versatile radionuclide or radiolabel, 99m-Technetium, having a gamma ray or photon energy in the region of 140 keV.

The resolution capabilities of gamma cameras incorporating scintillation detector crystals, inter alia, is limited both by the light coupling intermediate the detector and phototube matrix or array as well as by scatter phenomena of the gamma radiation witnessed emanating from within the in vivo region of investigation. Concerning the latter scattering phenomena, a degradation of resolution occurs from scattered photons which are recorded in the image of interest. Such photons may derive from Compton scattering into trajectories wherein they are caused to pass through the camera collimator and interact photoelectrically with the crystal detector at positions other than their point of in vivo derivation. Should such photon energy loss to the Compton interaction be less than the energy resolution of the system, it will effect an off-axis recordation in the image of the system as a photopeak photon representing false spatial information or noise. As such scattered photons record photopeak events, the noise increase and consequent resolution quality of the camera diminishes. For the noted desirable 140 keV photons, the scintillation detector type camera energy resolution is approximately 15 keV. With this resolution, photons which scatter through an angle from 0° to about 70° will be seen by the system as such photopeak events.

A continuing interest in improving the resolution qualities of gamma cameras has lead to somewhat extensive investigation into imaging systems incorporating relatively large area semiconductor detectors. Such interest has been generated principally in view of theoretical indications of an order of magnitude improvement in statistically limited resolution to provide significant improvements in image quality. In this regard, for example, reference may be made to the following publications:

II. R. N. Beck, L. T. Zimmer, D. B. Charleston, P. B. Hoffer, and N. Lembares, "The Theoretical Advantages of Eliminating Scatter in Imaging Systems", Semiconductor Detectors in Nuclear Medicine, (P. B. Hoffer, R. N. Beck, and A. Gottschalk, editors), Society of Nuclear Medicine, New York, 1971, pp. 92–113.

III. R. N. Beck, M. W. Schuh, T. D. Cohen, and N. Lembares, "Effects of Scattered Radiation on Scintillation Detector Response", Medical Radioisotope Scintigraphy, IAEA, Vienna, 1969, Vol. 1, pp. 595–616.

IV. A. B. Brill, J. A. Patton, and R. J. Baglan, "An Experimental Comparison of Scintillation and Semiconductor Detectors for Isotope Imaging and Counting", IEEE Trans. Nuc. Sci., Vol. NS-19, No. 3, pp. 179–190, 1972.

V. M. M. Dresser, G. F. Knoll, "Results of Scattering in Radioisotope Imaging", IEEE Trans. Nuc. Sci., Vol. NS-20, No. 1, pp. 266–270, 1973.

Particular interest on the part of investigators has been paid to detectors provided as hybridized diode structures formed basically of germanium. To derive discrete regions for spatial resolution of impinging radiation, the opposed parallel surfaces of the detector diodes may be grooved or similarly configured to define transversely disposed rows and columns thereby providing identifiable discrete regions of radiation response. Concerning such approaches to treating the detectors, mention may be made of the following publications:

VI. J. Detko, "Semiconductor Dioxide Matrix for Isotope Localization", Phys. Med. Biol., Vol. 14, No. 2, pp. 245–253, 1969.

VII. J. F. Detko, "A Prototype, Ultra Pure Germanium Orthogonal Strip Gamma Camera," Proceedings of the IAEA Symposium on Radioisotope Scintigraphy, IAEA/SM-164/135, Monte Carlo, October 1972.

VIII. R. P. Parker, E. M. Gunnerson, J. L. Wankling, and R. Ellis, "A Semiconductor Gamma Camera with Quantitative Output," Medical Radioisotope Scintigraphy.

IX. V. R. McCready, R. P. Parker, E. M. Gunnerson, R. Ellis, E. Moss, W. G. Gore, and J. Bell, "Clinical Tests on a Proto type Semiconductor Gamma-Camera," British Journal of Radiology, Vol. 44, 58-62, 1971.

X. Parker, R. P., E. M. Gunnerson, J. S. Wankling, R. Ellis, "A Semiconductor Gamma Camera with Quantitative Output," Medical Radioisotope Scintigraphy, Vol. 1, Vienna, IAEA, 1969, p. 71.

XI. Detko, J. F., "A Prototype, Ultra-Pure Germanium, orthogonal-Strip Gamma Camera," Medical Radioisotope Scintigraphy, Vol. 1, Vienna, IAEA, 1973, p. 241.

XII. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in IEEE Trans. Nucl. Sci., Vol. NS-21, No. 1 February 1974, p. 658.

XIII. Owen, R. B., M. L. Awcock, "One and Two Dimensional Position Sensing Semiconductor Detectors," IEEE Trans. Nucl. Sci., Vol. NS-15, June 1968, p. 290.

In the more recent past, investigators have shown particular interest in forming orthogonal strip matrix detectors from p-i-n semiconductors fashioned from an ultra pure germanium material. In this regard, reference is made to U.S. Pat. No. 3,761,711 as well as to the following publications:

XIV. J. F. Detko, "A Prototype, Ultra Pure Germanium, Orthogonal Strip Gamma Camera," Proceedings of the IAEA Symposium on Radioisotope Scintigraphy, IAEA/SM-164/135, Monte Carlo, October, 1972.

XV. Schlosser, P. A., D. W. Miller, M. S. Gerber, R. F. Redmond, J. W. Harpster, W. J. Collis, W. W. Hunter, Jr., "A Practical Gamma Ray Camera System Using High Purity Germanium," presented at the 1973 IEEE Nuclear Science Symposium, San Francisco, November 1973; also published in IEEE Trans. Nucl. Sci., Vol. NS-21, No. 1, February 1974, p. 658.

High purity germanium detectors promise numerous advantages both in gamma camera resolution as well as practicality. For instance, by utilizing high purity germanium as a detector, lithium drifting arrangements and the like for reducing impurity concentrations are avoided and the detector need only be cooled to requisite low temperatures during its clinical operation. Readout from the orthogonal strip germanium detectors is described as being carried out utilizing a number of techniques, for instance, each strip of the detector may be connected to a preamplifier-amplifier channel and thence directed to an appropriate logic function and visual readout. In another arrangement, a delay line readout system is suggested with the intent of reducing the number of preamplifiers-amplifier channels, and a technique of particular interest utilizes a charge splitting method. With this method or technique, position sensitivity is obtained by connecting each contact strip of the detector to a charge dividing resistor network. Each end of each network is connected to a virtual earth, charge sensitive preamplifier. When a gamma ray interacts with the detector, the charge released enters the string of resistors and divides in relation to the amount of resistance between its entry point in the string and the preamplifiers. Utilizing fewer preamplifiers, the cost and complexity of such systems is advantageously reduced. A more detailed description of this readout arrangement is provided in:

XVI. Gerber, M. S., Miller, D. W., Gillespie, B., and Chemistruck, R. S., "Instrumentation For a High Purity Germanium Position Sensing Gamma Ray Detector," IEEE Trans. on Nucl. Sci., Vol. NS-22 No. 1, February, 1975, p. 416.

To achieve requisite performance and camera image resolution, it is necessary that substantially all sources of noise or false information within the system be accounted for. In the absence of adequate noise resolution, the performance of the imaging systems may be compromised to the point of impracticality. Until the more recent past, charge-splitting germanium detector arrangements have not been considered to be useful in gamma camera applications in consequence of thermal noise anticipated in the above-noted resistor divider networks, see publication VII, supra. However, as will be evidenced in the description to follow, such considerations now are moot.

Another aspect in the optimization of resolution of the images of gamma cameras resides in the necessarily inverse relationship between resolution and sensitivity. A variety of investigations have been conducted concerning this aspect of camera design, it being opined that photon noise limitations, i.e. statistical fluctuations in the image, set a lower limit to spatial resolution. Further, it has been pointed out that the decrease in sensitivity witnessed in conventional high resolution collimators may cancel out any improvements sought to be gained in image resolution. A more detailed discourse concerning these aspects of design are provided, for instance, in the following publications:

XVII. E. L. Keller and J. W. Coltman, "Modulation Transfer and Scintillation Limitations in Gamma Ray Imaging", J. Nucl. Med. 9, 10, 537–545 (1968)

XVIII. B. Westerman, R. R. Sharma, and J. F. Fowler, "Relative Importance of Resolution and Sensitivity in Tumor Detection", J. Nucl. Med. 9, 12 638–640 (1968)

Generally, the treatment of the signals derived at the entrance detection portion of gamma cameras involves a form of spatial or coordinate identification of photons reaching the detector and additionally, a form of analysis of the energy of radiation reaching the detector. Spatial analysis may be carried out by difference summing circuits, while energy determination is carried out by additive summing circuits. Further, pulse height analyzers may be utilized as one discriminating component of a system for determining the presence of true or false imaging information. In any of the systems both treating noise phenomena and seeking a high integrity of spatial information, a control is required which carries out appropriate noise filtering while segregating true from false information. In addition to the foregoing, it is necessary that the "through-put rate" of the system be maximized in order that it may accommodate a highest number of bits or pulses representing spatial and energy data. Of course, while carrying out such functions, the control arrangements for gamma camera systems must remain practical in terms of their complexity and consequent cost.

SUMMARY

The present invention is addressed to an improved gamma camera system of a variety utilizing a solid state strip array type detector. Coupled with the strips of the detector are impedance components; for instance, resistors which, in turn, represent the discrete elements of impedance networks. By operating upon the outputs of these networks through preamplification stages and the like, signals relating the spatial disposition and energy of photons interacting with the solid state detector are established. The invention observes that the receipt of charges at the output of the detecting arrangement is time variant in nature in correspondence with the position of interaction therewith of a given gamma ray. Accordingly, by virtue of its electrical parameters, the detector system exhibits a collection time constant $\tau_D$. The invention further considers that, with subtractive summation spatial derivation techniques as well as through the utilization of Gaussian and trapezoidal filtering of the spatial signals, improved camera system performance is realized. In particular, trapezoidal shaping is carried out through the utilization of gated integrated circuits which are controlled in accordance with the invention, to achieve requisite integration over a period, $t_s$, corresponding with a value equivalent to about one-eighth of the noted time constant of the detector system, $\tau_D$. The energy analysis of a given spatial quantum of information is provided through summing arrangements associated with the noted impedance network outputs which are addressed to evaluating components serving, in turn, to analyze the peak energy values of the signals over a time, $t_e$.

An important aspect and object of the invention provides a control arrangement wherein the interval of energy analysis, $t_e$, is greater than the noted spatial period of integration, $t_s$, and the readout of the system is selectively enabled only with the derivation of an energy value for a given quantum of spatial information falling within predetermined upper and lower energy limits. These limits are selected to optimize the integrity or validity of the imaging content of radiation impinging upon the noted detector system.

As another object and aspect of the invention, an improved gamma camera type imaging system is provided of a variety utilizing a solid state detector arrangement in combination with impedance readout networks wherein the spatial signal output thereof is subtractively summed and integrated, as noted above, over an interval $t_s$. The latter interval is selected as about equal to or greater than one-eighth the collection time constant, $\tau_D$, or the solid state detector arrangement. Preferably, the summing arrangement includes stages providing for a Gaussian pulse shaping of the output of the detector as it is collected from preamplification stages.

The invention further contemplates, as an object, the provision of an improved imaging system for gamma cameras and the like, wherein the output of a solid state detector and impedance network, having been amplified, is appropriately directed to a summing arrangement which additively sums the outputs of the amplifier and which includes a high pass filtering stage or the like, which derives a time derivative signal of the noted summed output signals. The system further includes a comparator arrangement which responds to the value of each of the summing function derivative signal outputs as that signal equals or exceeds a predetermined reference value. Where such value for the derivative signal does so exceed the reference value, a start output is evolved by the comparator to which the control arrangement of the gamma camera system responds to commence the analysis of the initial quantum of information evolved at the solid state detector stages of the camera. Subsequent to this initial evaluation of an input quantum of information, the inventive control system is configured and arranged to terminate an operational cycle in the absence of an appropriate evaluation of the peak energy of the noted summed input signal. Should such peak energy not fall within the confines of a given window or energy range, the control system performs in short cycle manner to reset its analyzing components and, thereby, improve the pass-through rate and general performance of the imaging system.

As another object, the invention contemplates improvements for a system for imaging the distribution of a radiation-emitting isotope, such system including solid state detectors having charge characterized outputs representative of the energy and spatial disposition of corresponding interactions of the noted radiation with the detectors. Amplified outputs from the detectors are utilized for deriving output signals treated first by a summing function, serving to generate spatial signals, and an additional summing function deriving energy related signals of values corresponding with the energy values of the output of the initial summing function. The summing function achieving energy related data also incorporates a stage deriving the time derivative of the energy value of the amplified output signals. Through the utilization of an evaluating circuit, for instance, a single channel analyzer or the like, the peak values of the energy related signals are analyzed over a time, $t_e$, and this function provides a select output when that peak value of the energy signal lies within predetermined limits. The system further incorporates readout functions which receive an appropriately treated spatial signal to derive output information for clinical usage and the like. This system further incorporates a comparative arrangement which responds to the value of the noted summing stage derivative signal equalling or exceeding a predetermined reference value, for deriving a start output. In response to this start output, the control of the system commences signal treatment and evaluation of the spatial components of the input information from the detector and summing functions. Accordingly, a low level analysis of each input is derived. By maintaining a logic level corresponding with an ongoing analysis of a given spatial signal, a lock-out feature preventing the partial integration of spatial pulses too closely associated in time is avoided. Further, the display of spatial pulses which overlap is prevented through the association of energy information evaluation and spatial information evaluation. If two or more gamma arrays photoelectrically interact with the detector and their total energy is absorbed in a time less than the integration interval, the energy pulse peak value will not fall within the evaluation window or select range and the control system will react to effect the carrying out of a shortened or aborting cycle. Consequently, the camera control system affords a more efficient treatment of information derived from a radiation source of clinical interest.

Other objects of the invention will, in part, be obvious and will, in part, appear hereinafter.

The invention, accordingly, comprises the system and apparatus possessing the construction, combination of elements, and arrangement of parts which are exemplified by the following detailed disclosure.

For a fuller understanding of the nature and objects of the invention, reference should be had to the following detailed description taken in connection with the accompanying drawings.

DETAILED DESCRIPTION

Figure 1:
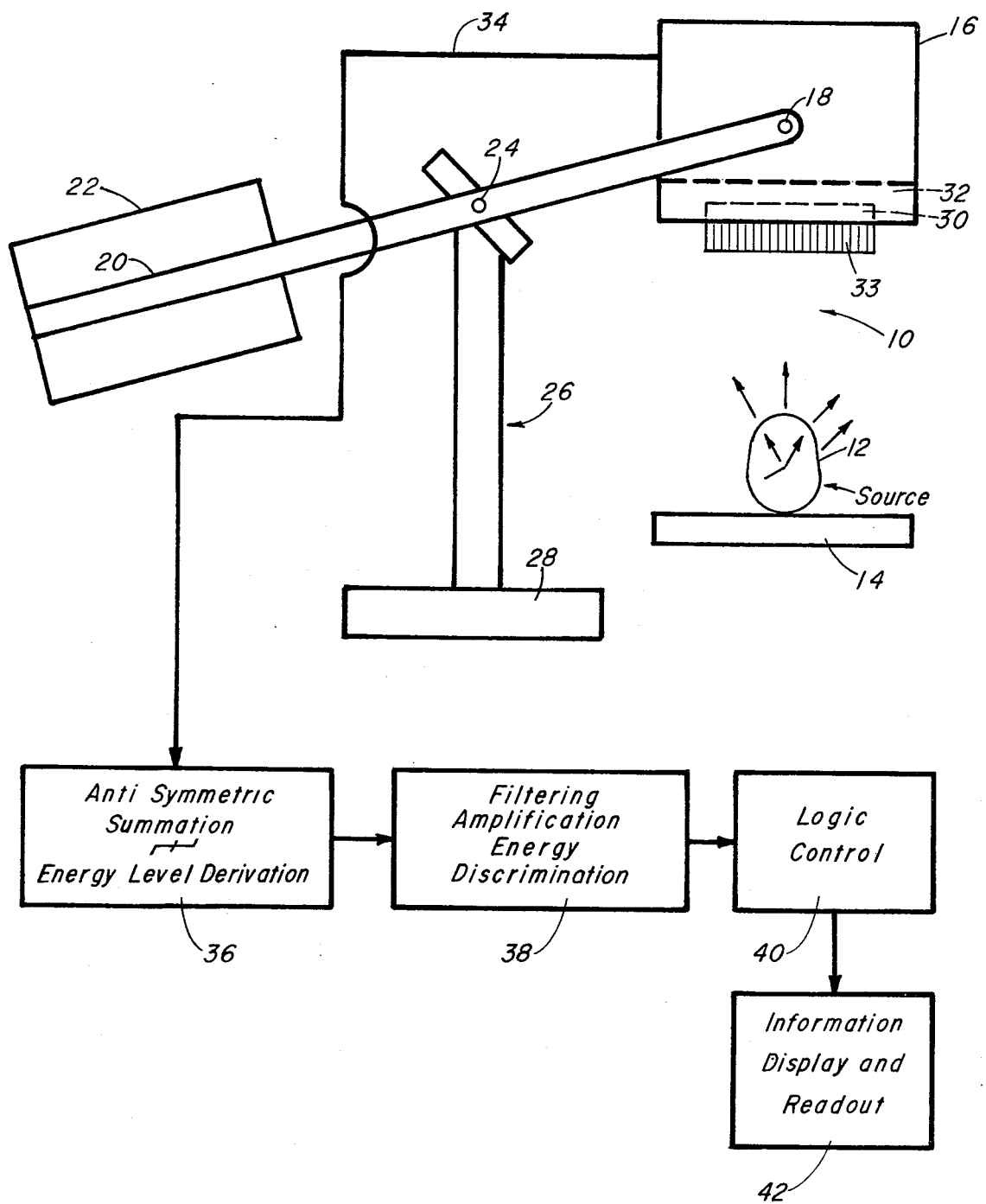
FIG. 1 is a schematic representation of a gamma camera arrangement as may utilize the improvements of the invention, showing, in block schematic form, control functions of the system.

During contemplated clinical utilization, a camera according to the instant invention is used to image gamma radiation radiopharmaceutically derived from a region within a patient. Looking to FIG. 1, an exaggerated schematic representation of such a clinical environment is revealed generally at 10. Environment 10 schematically displays the cranial region of interest 12 of a patient to whom has been administered a radio-labeled pharmaceutical, which will have tended to concentrate within that region. Accordingly, radiation is depicted as emanating from this cranial region 12 of the patient as the latter is positioned upon some supporting platform, as at 14. Over the region 12 is positioned the head or housing 16 of a gamma camera. Housing 16 is pivotally supported at 18 from a beam 20. Beam 20, carrying a counter-weight 22, is pivotally supported at 24 in dual axis gimbal fashion from an upstanding support 26. Support 26 is fixedly attached to and extends from a base member 28.

As is represented only in dotted line and generalized fashion, housing 16 is configured to retain an ultra-pure germanium orthogonal strip type semi-conductor detector 30 as well as impedance resistor-divider networks tapping the detector and, additionally, preamplification stages (not shown in FIG. 1) within a vacuum chamber 32. Chamber 32 is retained at a predetermined low temperature, for instance about 77 degrees K by an appropriate cryogenic system during operation of housing 16, for purposes of providing one aspect of detector and electronic noise control and diminution. Adjacent to the detector 30 and disposed intermediate the detector and the patient-retained source of radiation 12, is a multi-channel collimator 33, the particular design aspects of which are revealed in detail in a copending application for the United States patent by P. A. Schlosser et al., Ser. No. 656,304 entitled: "Gamma Ray Camera for Nuclear Medicine", filed Feb. 9, 1976 by P. A. Schlosser and J. W. Steidley, and assigned in common herewith.

During operation of the camera, that radiation emanating from source 12 is spatially coded initially at collimator 33 by attenuating or rejecting off-axis radiation representing false information. That radiation passing collimator 33 impinges upon detector 30 and a significant portion thereof is converted to discrete charges or image signals. Detector 30 is so configured as to distribute these signals to appropriate impedance networks as well as select preamplification stages retained within chamber 32 to provide initial signals representative of image spatial information, along conventional coordinate axes, as well as signals representing values for radiation energy levels. By virtue of the particular collimator structure, as well as the orthogonal striptype detectors as are utilized, respectively, at 33 and 30, the image information assembled at the entrance or acceptance arena of housing 16 can be considered somewhat digital in nature. That is, with the absence of noise considerations and the like, to be considered in more detail hereinafter, such information would be derived as a spatially distributed collection of dots which the eye of the clinical operator would be called upon to synthesize. By appropriately treating the spatial information, however, image synthesis is optimized for the resolution available within the camera system.

Data from the detector 30, resistor chains and associated preamplification stages then is introduced, as represented schematically by line 34, to filtering and logic circuitry which operates thereupon to form an image of optimized resolution and veracity. As noted earlier, ideally, such information should approach the theoretical imaging accuracy of the camera system, as derived from the geometry of the detector structure 30 and collimator arrangement 33, as well as it is formed in view of the limitations of the electronic filtering, amplification and control of the system.

Image spatial and energy level signals from line 34, initially, are introduced into anti-symmetric summation and energy level derivation functions represented at block 36. The antisymmetric summation carried out at block 36 operates upon the charges directed into the earlier noted resistive chains or networks associated with the orthogonal logic structuring of detector 30 to derive discrete signals or voltage values corresponding with image element location. Additionally, circuitry of the function block 36 derives a corresponding signal representing the energy level of the incident gamma radiation. The output of block 36 is directed to a filtering amplification and energy discrimination function as represented at block 38. Controlled from a logic control function shown at block 40, function 38 operates upon the signal input thereto to accommodate the system to parallel and serially defined noise components through the use of Gaussian amplification or filtering, including trapezoidal pulse shaping of data representing the spatial location of image bits or signals. Similarly, the energy levels of incoming signals are evaluated, for instance, utilizing single channel analyzer components controlled by logic 40, to establish an energy level window for data received within the system. In this regard, signals falling above and below predetermined energy levels are considered false and are blocked. From amplification and discrimination stage 38 and logic control 40, the analyzed signals are directed into an information display and readout function, as is represented at block 42. Components within function block 42 will include display screens of various configurations, image recording devices, for instance photographic apparatus of the instant developing variety, radiation readout devices and the like, all of which are controlled at the option of the system operator.

Figure 2:
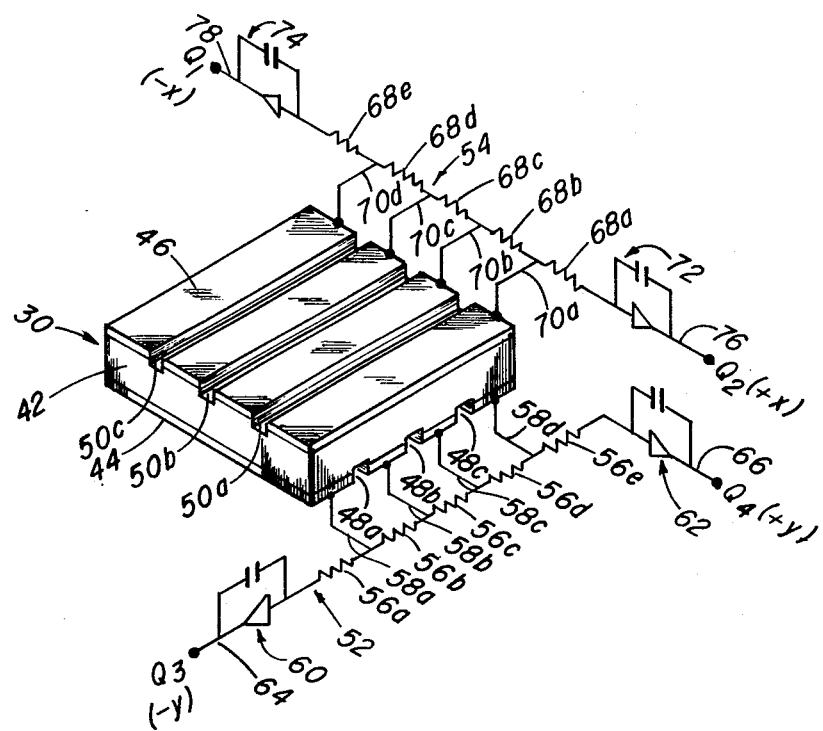
FIG. 2 is a pictorial representation of a solid state orthogonal strip high purity germanium detector incorporating a charge splitting resistor network in combination with preamplification electronics.

Turning to FIG. 2, an exaggerated pictorial representation of a portion of detector 30 and its associated impedance network readout is revealed.

Detector 30 is fabricated from p-type high purity germanium by depositing an n-type contact, for instance, lithium, on one face and a p-type contact, for instance, palladium, on the opposite face of a rectangular planar crystal. Accordingly, a high purity germanium region of the crystal, as at 42, serves as an intrinsic region between p-type semi-conductor region contacts 44 and n-type semi-condutor region contacts as at 46. The intrinsic region 42 of the p-i-n detector forms a region which is depleted of electrons and holes when a reverse bias is applied to the contacts. Grooves as at 48a-48c are cut into the continuous p-type contact or region at one face of the detector to form strips of isolated p-type semiconductor material. On the opposite face of the detector, orthogonally disposed n-type semiconductor strips similarly are formed through the provision of grooves 50a-50c. Configured having this geometry, the detector 30 generally is referred to as orthogonal strip detector or an orthogonal strip array semiconductor detector. The electrode strips about each of the opposed surfaces of detector 30, respectively, are connected to external charge splitting resistor networks revealed generally at 52 and 54. Resistor network 52 is formed of serially coupled resistors or impedance components 56a-56e which, respectively, are tapped at their regions of mutual interconnection by leads identified, respectively, at 58a-58d extending, in turn, to appropriate ones of the orthogonal strips. The opposed ends of network 52 terminate in preamplificaion stages 60 and 62, the respective outputs of which at 64 and 66 provide spatial output data for insertion within the above-noted summation and energy level derivation function 36 to provide one orthogonal or coordinate output, for instance, designated as a y-axis signal.

In similar fashion, network 54 is comprised of a string of serially coupled resistors or impedance components 68a-68e, the mutual interconnections of which are coupled with the electrode strips at surface 46, respectively, by leads 70a-70d. Additionally, preamplification stages as at 72 and 74 provide outputs, respectively, at lines 76 and 78 carrying data or signals representative of image information along an x-axis or axis orthogonally disposed with respect to the output of network 52.

With the assertion of an appropriate bias over detector, as described in the noted U.S. Pat. No. 3,761,711, any imaging photon absorbed therewithin engenders ionization which, in turn, creates electron-hole pairs. The charge thusly produced is collected on the orthogonally disposed electrode strips by the bias voltage and such charge flows to the corresponding node of the impedance networks 52 and 54. Further, this charge divides in proportion to the admittance of each path to the virtual ground input of the appropriate terminally disposed preamplification stage. Such charge-sensitive preamplification stage integrates the collected charge to form a voltage pulse proportional to that charge value. Assigning charge value designations $Q_1$ and $Q_2$, respectively, for the outputs 78 and 76 of network 54, and $Q_3$ and $Q_4$, respectively, for the output lines 64 and 66 of network 52, the above-noted Summation and Energy Level Derivation functions for spatial and energy data may be designated. In this regard, the x-position of each diode defined by the orthogonal strip geometry is found to be proportional to $Q_1$, $Q_2$, and their difference, i.e. $(Q_1-Q_2)$, and the y-position is proportional to $Q_3$, $Q_4$, and their difference, i.e. $(Q_3-Q_4)$. The energy of the incident gamma ray is proportional to $Q_1+Q_2$, and $(Q_3+Q_4)$, and $[(Q_1+Q_2) - (Q_3+Q_4)]$, or in the latter expression, $[(Q_3+Q_4) - (Q_1+Q_2)]$.

As has been alluded to earlier herein, the orthogonal strip position-sensitive detector is resolution limited by the noise associated with the detector as well as the charge dividing network. Consequently, it is necessary to consider the noise characteristics of the system from the standpoint of minimizing the effects thereof upon resolution as well as treating such phenomena to derive desired imaging effects. Generally, it may be concluded that the resistor network is the dominant source of noise within the spatial channel of the system, while the resistor network, coupled with the detector leakage current, represents the dominate noise source in the system's energy channel. As will become more apparent as the instant description unfolds, spatial noise dominantly is electrically parallel in nature, whereas energy channel noise may be considered of an electrically series variety.

Figure 3:
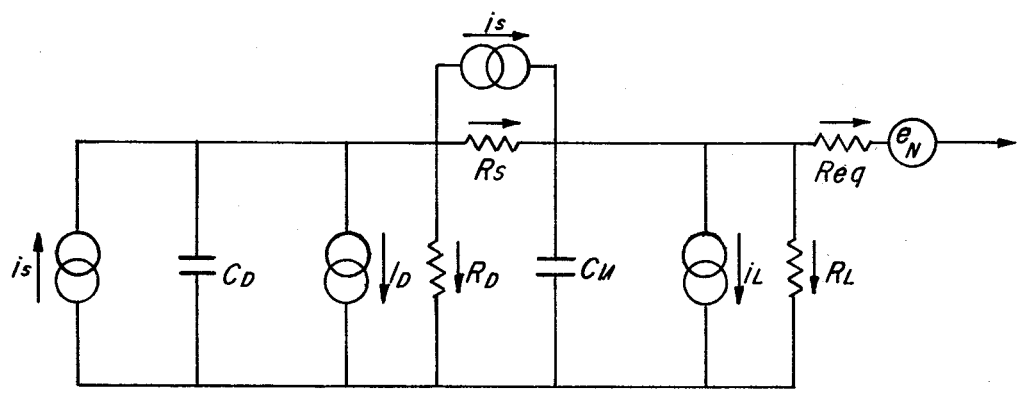
FIG. 3 is an equivalent noise model circuit for solid state detectors as utilized in accordance with the instant invention.

Noise is the random fluctuation of the preamplifier output voltage when there is no stimulus. It is generated by imperfections in the preamplifier input device, thermal movement of charge carriers in the resistors and the bulk of the detector and imperfections in the crystal structure of the detector. Looking to FIG. 3, an equivalent noise model circuit for solid state detectors is revealed. Note that the model reveals a detector leakage current, $i_D$, which is assumed to be formed of individual electrons and holes crossing the depletion layer of the detector. Such electron hole pairs are thermally generated in the depletion layer. Resistive elements which are in parallel with the system input capacitance, $C_{IN}$, generate thermal noise which is integrated by this capacitance and appears at the preamplifier input as a step function. The system input capacitance is the parallel combination of stray capacitance at the preamplifier input and the feedback capacitor of the preamplifier. Those resistive components which contribute to this noise term are the high voltage bias resistor, the preamplifier feedback resistor and the detector bulk resistance. For a charge dividing resistive strip network, a portion of the dividing resistance, $R_D$, is in parallel with the detector capacitance. Sice $R_D$ is less than one hundred kilo-ohms, it represents a significant noise source. The thermal noise from resistors in series with the detector capacitance appears as a delta function to the preamplifiers. For spectroscopy systems, this resistance is minimized and the noise source is neglected. The noise developed by the preamplifier input stage is modeled using a resistor, $R_{eq}$. Finally, a noise term which is not shown in FIG. 3 is "flicker" noise caused by structural changes and surface effects in the conduction material of the noted preamplifier input stage. This noise aspect generally is considered to be insignificant.

Since the noise sources discussed above have a uniform power spectral density, bandwidth limiting filtering or pulse shaping generally is considered appropriate for maximizing the signal to noise ratio of the system. As suggested earlier, the fundamental noise sources are classifiable as two types, parallel noise representing the charge due to the electron flow which is integrated by the input circuit capacitance, and series noise representing the charge due to the electron flow which is not integrated by input capacitance. These noise sources are considered to be mutually related in terms of filtering to the extent that as efforts are made to diminish one, the other increases. The high frequency component noise generally is considered a series type while low frequency noise is considered of the parallel variety. As has been detailed in the publications given above, the use of Gaussian and the Gaussian-trapezoidal noise filtering circuits has been found to optimize the energy and spatial resolution values of the camera system.

Figure 4:
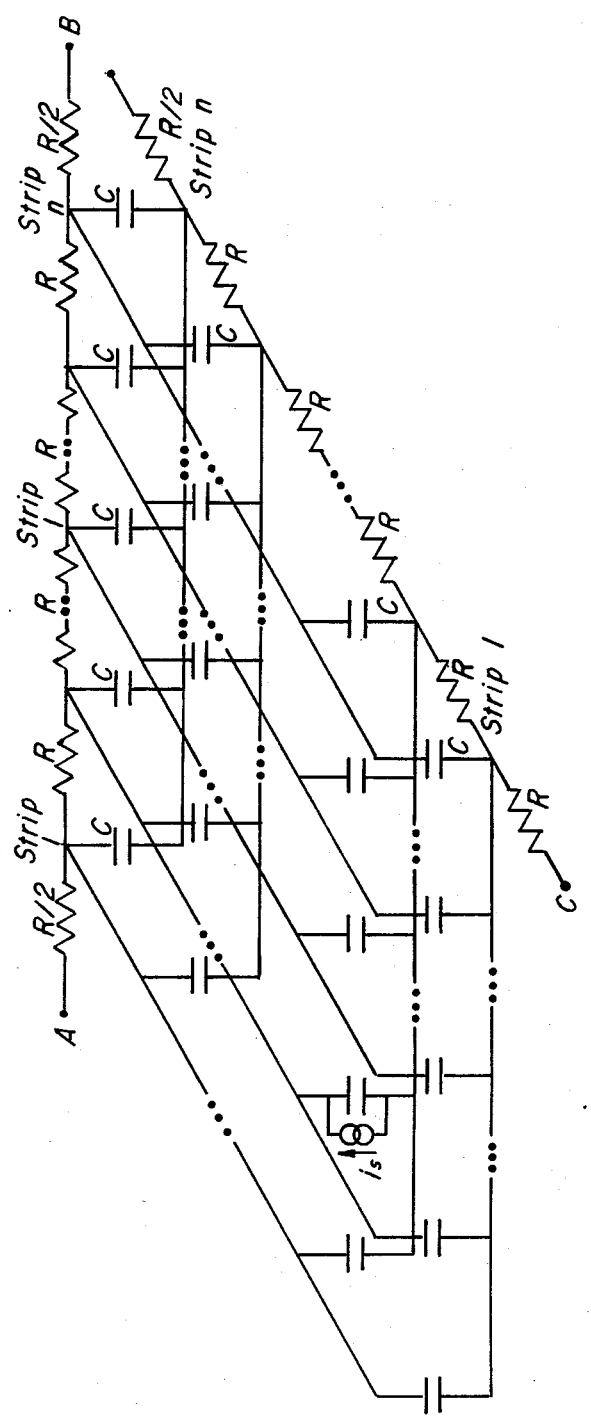
FIG. 4 is a circuit model of a detector and related resistor network, schematically representing the position-sensitive detector arrangement of the invention.

Turning now to FIG. 4, a circuit model of the detector 30 and the resistor networks is portrayed. The discrete nature of the detector system and the method of readout is revealed in the figure with the discrete capacitors forming an $n \times n$ array. Each row and column is defined by the charge measured at the end of the resistor strings. The electron-hole pairs which are formed when a gamma ray interacts with the detector are collected on opposite surfaces. A charge enters the resistive network and flows to terminal A or B (C or D) in relation to the resistance between its entry point and the virtual earth terminal of each preamplifier (FIG. 2). The intersection of the column and row defines the diode position in which the gamma ray energy was deposited. Note in the figure, that individual capacitances are represented which are exemplary of the inherent capacitance of the detector itself. When considered in conjunction with the resistor networks as revealed in the figure, it may be noted that a particular time constant or interval is required for any impinging charge to be represented by a charge flow to the output taps of the resistor chains. Accordingly, the system must provide an adequate time interval or time constant, $\tau_D$, for this charge flow to avoid error in information collection. In effect, it may be assumed that the detector and each of the resistor strings of the noted impedance networks respond as a diffusive line, and the peaking time of the preamplifier output pulses will vary as a function of the position of interaction, $x_O$, of an incident gamma ray. The voltage output of each preamplifier (FIG. 2) due to the instantaneous transfer of charge $Q_O$ at position $x_O$ is:

$$V(0,x_o,t) = \frac{Q_o}{C_f}\left[1 - \frac{x_o}{L} - \sum_{m=1}^{\infty} \frac{2}{m\pi} \sin\left(\frac{m\pi x_o}{L}\right) \exp\left[-\frac{m^2\pi^2 t}{\tau_D}\right]\right], \quad (1)$$

$$V(L,x_o,t) = \frac{Q_o}{C_f}\left[\frac{x_o}{L} + \sum_{m=1}^{\infty} \frac{2}{m\pi} \cos(m\pi)\sin\left(\frac{m\pi x_o}{L}\right)\exp\left[\frac{-m^2\pi^2 t}{\tau_D}\right]\right], \quad (2)$$

where $C_f$ is the feedback capacitance of a preamplifier in farads, L is a given linear dimension of the detector, $\tau_D$ is the time constant of the detector (i.e. $\tau_D = 2R_D C_D$), $x_o$ defines the position of interaction and $m$ is a summation variable.

Examination of equations (1) and (2) show that for a time $$t \geq \frac{\tau_D}{2}, \quad (3)$$

i.e., an output generation time equivalent to one half of the time constant of the detector, the value of $V(0,x_o,t)$ is within 1% of its final value for all $x_o/L < 0.95$ and $V(L,x_o,t)$ is within 1% of its final value for all $x_o/L > 0.05$. Stated otherwise, the error generated from ballistic deficit type characteristics of the system, as it relates to the energy of one preamplifier readout diminishes to a value of 1% within a period of one half the time constant, $\tau_D$ of the detector.

By subtracting the output of the one preamplifier of a network, i.e. at the $x = L$ position from the corresponding amplifier output at the $x = O$ position, i.e.

$$V(0,x_o,t) - V(L,x_o,t) = \frac{Q_o}{C_f}\left[1 - \frac{2x_o}{L} - \right. \quad (4)$$

$$\sum_{m=1}^{\infty} \frac{2}{m\pi} \sin\left(\frac{m\pi x_o}{L}\right)$$

$$\left. (1 + \cos m\pi)\exp\left(\frac{-m^2\pi^2 t}{\tau_D}\right)\right],$$

the following important observations may be observed. Equation (4) shows that as the spatial location of information impingement alters from O to L, the resulting voltage readout moves from a positive unit value to a negative unit value. Stated otherwise, the output signal derived from the above signal treatment subtractive approach ranges from $+ Q_o/C_f$ at $x_o=0$ to $-Q_o/C_f$ at $x_o = L$, making the signal twice that of earlier suggested one preamplifier collection technique. Further, it may be observed that the odd numbered series terms vanish, thereby reducing the position signal peaking time. The value of equation (4) is within 1% of its final value for all values $x_o/L \leq 0.45$ and $x/L \geq 0.55$ after a time $$t \geq \frac{\tau_D}{8}. \quad (5)$$

Accordingly, it may be observed that through the utilization of a dual preamplifier subtractive or "antisymmetric" method of signal analysis, the necessary time constant related signal treatment within the spatial channel is diminished by a factor of 4.

Turning now to the conditions obtaining within the energy channel of the system, the energy channel is derived by summing the output of each preamplifier to obtain the voltage pulse:

$$V(0,x_o,t) + V(L,x_o,t) = \frac{Q_o}{C_f}\left[1 - \right. \quad (6)$$

$$\sum_{m=1}^{\infty} \frac{2}{m\pi} \sin\left(\frac{m\pi x_o}{L}\right)$$

-continued $$(1 - \cos m\pi) \exp\left(\frac{-m^2\pi^2 t}{\tau_D}\right)\bigg]$$

Note again, that the peaking time of the pulse is position dependent. At $x_o/L = 0.5$, the maximum peaking time occurs and the pulse is within 1% of its final value at $t = \tau D/2$. Accordingly, it may be observed that ballistic deficit or charge collection type considerations within the energy channel will require a charge collection period, for practical purposes, equivalent to one half of the time constant of the detector.

Now considering noise phenomena, as earlier discussed in combination with ballistic deficit considerations, as derived immediately hereinabove, dominant spatial noise, which is parallel noise, may be expressed as follows:

$$N_{qSI} = \frac{1}{q}\left(\frac{4kT_D a_p \tau_o}{R_D}\right)^{\frac{1}{2}} \quad (7)$$

where $N_{qSI}$ is the equivalent noise charge in number of electrons for one preamplifier spatial measurements, $R_D$ is the total resistance of the resistive chain, $T_D$ is the temperature of the detector and chain, $a_p$ is a weighting factor of the filter, $a$ is the magnitude of the charge on an electron, and $k$ is Boltzmans constant.

In the expressions given above, i.e. equations 1 through 7, the term $R_D$ is intended as the value representing the average of the total resistance of each resistive network. For the exaggerated exemplary detector shown in FIG. 2, the term $R_D$ represents one-half the sum of the resistance values of networks 52 and 54. Note from equation (7) that the noise is proportional to the square root of the temperature as well as the weighting factor and the time constant of the system. As disclosed earlier, this time constant is limited by the ballistic deficit conditions of the system. Note further that the noise is inversely proportional to total resistance of one chain or resistor network. Therefore, it is desirable for system efficiency to minimize the temperature under which it operates as well as the weighting factor and time constant and to elevate the resistance value to the extent practical. Equation (7) is for one preamplifier readout. Reconfiguring the equation to represent a subtractive or antisymmetric arrangement, the following expression obtains:

$$N_{qSAS} = \frac{2}{q}\left(\frac{4kT_D}{R_D} a_p \tau_o\right)^{\frac{1}{2}} \quad (8)$$

From this equation, note that a subtractive arrangement permits the ballistic deficit dictated time constant to reduce by a factor of 4, while the value of noise increases by a factor of 2 for that same time constant. However, since a reduced time constant (factor of 4) is involved in a subtractive arrangement, the noise value, otherwise increased by a factor of 2, remains the same and the signal-to-noise ratio is increased by a factor of 2. Recall the earlier discussion above, that the unit signal value runs from a positive unit to a negative unit within a subtractive system. The value $R_D$ is difficult to increase inasmuch as a concomitant reduction in energy resolution generally is witnessed for such alteration. Temperature drop can be achieved practically, and the weighting factor, $a_p$, can be altered to a more or less ideal value by appropriate selection of filtering systems. It has been determined that a 43.4 percent improvement in spatial resolution is realized if antisymmetric summation, i.e. subtractive summation, is used as opposed to the utilization, for instance, of one preamplifier for spatial measurement.

Looking additionally to the "ballistic deficit" phenomenon, for thin detectors, i.e. about 5 mm in thickness, the detector charge collection time is small and does not affect circuitry treating a detected signal. For thick detectors, however, i.e. having a thickness in the range of about 2 cm, the bulk charge collection time varies from approximately 100 to 200 nanoseconds. Since this collection time is approximately the same as the collection time of the charge dividing network, its contribution to ballistic deficit problems must be considered. For such systems, the optimum filtering arrangement consists of a time invariant pre-filter followed by a gated integrator circuit. Such filters generally are referred to as gated-integrators or trapezoidal filters. The filter preferred for the purpose is a Gaussian trapezoidal filter which consists of a time invariant Gaussian filter followed by a gated integrator circuit. Such arrangement is revealed in more detail in the disclosure to follow. For a detailed discourse concerning the utilization of antisymmetric summation as well as the utilization of trapezoidal filtering within the spatial channel of the system, reference is made to the following unpublished work:

XVI. Hatch, K. F., "Semiconductor Gamma Camera", Ph, D. Dissertation, Massachusetts Institute of Technology, Cambridge, Massachusetts, February, 1972.

The equivalent noise charge in number of electrons for Gaussian trapezoidal spatial measurements may be represented by the following expression:

$$N_{qSGT} = \frac{2}{q}\left(4kT_D a_p T_I \frac{1.79}{R_D}\right)^{\frac{1}{2}} \quad (9)$$

wherein $a_p$ is the parallel noise weighting function value for Gaussian trapezoidal systems and $T_I$ is the integration time. Analysis of the foregoing shows that an excellent improvement in spatial resolution is obtained by using antisymmetric Gaussian trapezoidal filtering. This improvement is realized because the effects of "ballistic deficit" are greatly reduced.

The corresponding equivalent noise charge in number of electrons for the energy channel of the system may be expressed by the following formulation:

$$N_{qESI} = \frac{1}{q}\left(2qi_D a_p \tau_o + 4kT_D \frac{R_D C_b^2 a_s}{6\tau_o}\right)^{\frac{1}{2}} \quad (10)$$

In accordance with the instant invention, an important aspect of the above energy channel and spatial channel analyses has been discovered. In this regard, it may be recalled that opposed relationships stem from a consideration of parallel vs. series noise phenomena. For instance, it may be recalled that energy noise is considered serial in nature whereas spatial noise is considered to be parallel in nature. The energy noise equation, as shown at (10) above, represents a straight summation of two preamplifier outputs and the initial parallel noise factor presented within the brackets thereof is of dismissable magnitude. When compared with the spatial noise equation (9) above, it may be observed that two separate time constant values, $\tau_o$, $\tau_3$, respectively, for spatial resolution and energy resolution may be incorporated within the circuitry treating the output of the system detector. For instance, the energy resolution filtering of the system requires a relatively extended time constant, whereas corresponding spatial filtering requires a relatively short one for highest signal to noise ratio considerations. Inasmuch as the outputs of the filtering media reach the output displays of the camera or imaging system simultaneously, any multiple pulse errors introduced into the longer time constant energy filter individually will be integrated to achieve a peak value above a predesignated window function of the energy channel (block 38, FIG. 1). Accordingly, false information generated from pulse pile-up phenomena and the like may be rejected without recourse to more involved discrimination circuitry. Such a desired system circuit arrangement will be revealed in the description of the control system to follow.

Figure 5:
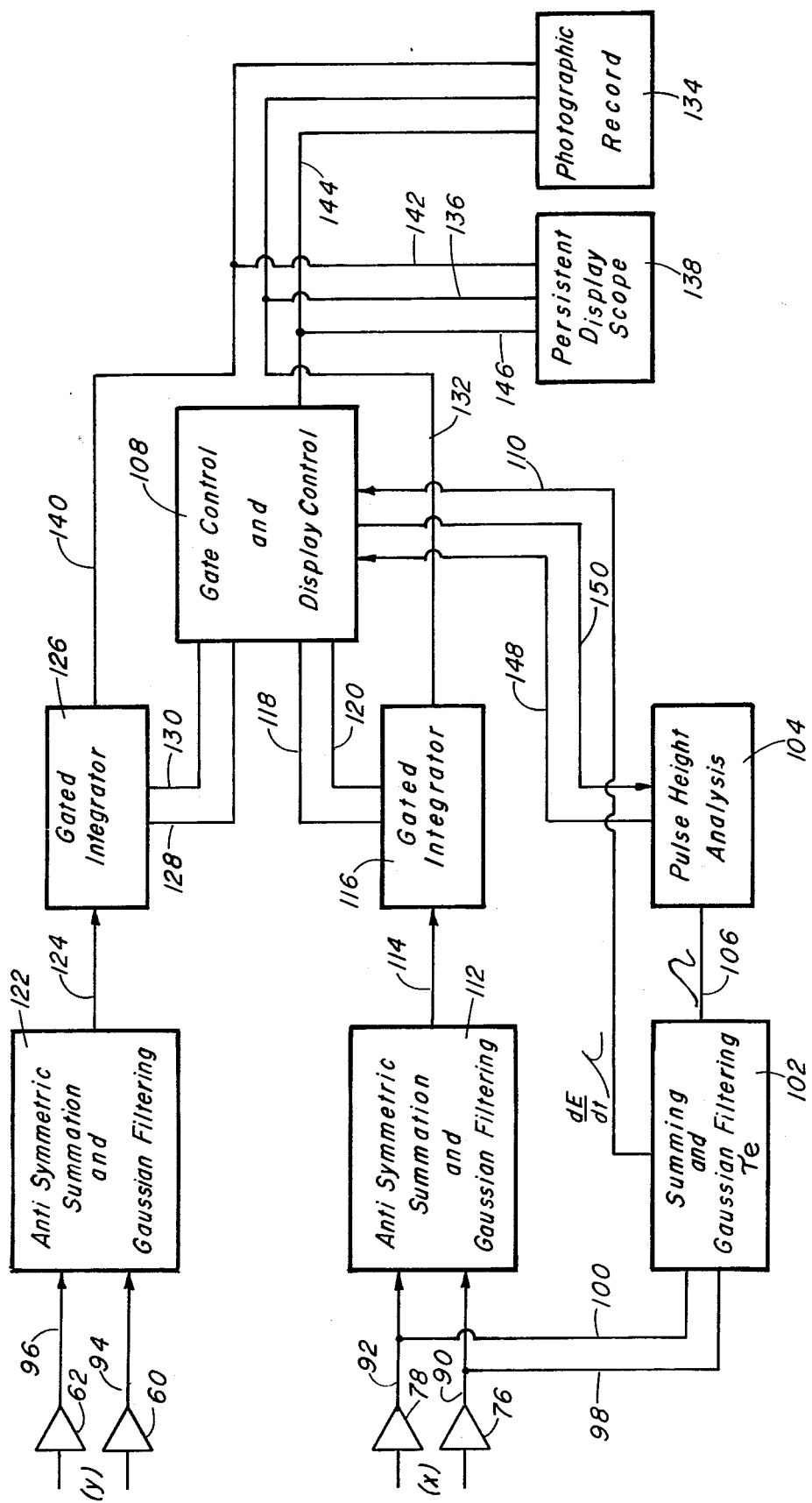
FIG. 5 is a block schematic diagram of a control system configured according to the invention.

Referring now to FIG. 5, a block schematic representation of the control system for the gamma camera is presented. In the figure, preamplification stages 76, 78 and 60, 62 are reproduced and the outputs thereof, respectively, are revealed at lines 90-96 Arbitrarily designating, for instance, preamplifier 76 and 78 as deriving energy information along an x-axis, the outputs thereof at 90 and 92 are coupled, respectively, through lines 98 and 100 to the input of a Summing and Gaussian Filtering function 102. As discussed in detail above, function 102 operates under a relatively extended time constant, identified within the block as $\tau_e$. One output from function 102 is directed to a pulse height analysis function 104 from along line 106. The other output of function 102 is directed to a Gate Control and Display Control function 108 from along line 110. This is an energy derivative pulse, as identified at line 110, and provides a start pulse input to function 108. Output lines 90 and 92 also provide the spatial channel input to Antisymmetric Summation and Gaussian Filtering function 112. From function 112, a subtractive filtered signal is directed along line 114, to a Gated Integrator 116 operating under an integrating period corresponding with time constant $\tau_o$. Control into gated integrator, for instance, establishing the time constant value, $\tau_o$, emanates from gate control function 108 through line 118. Additionally, a reset control is provided to the integrator from line 120.

Similar to the x-axis spatial channel inputs, the y-axis spatial channel inputs deriving through lines 94 and 96 are introduced into an Antisymmetric Summation and Gaussian Filtering function shown at block 122. The output from block 122, as is present at line 124, is introduced to a Gated Integrator function 126, structured identically to Gated Integrator function 116. Time constant $\tau_o$ control over integrator 126 is asserted from gate control function 108 through line 128, while reset control is asserted from line 130. The outputs from the x-axis Gated Integrator Function 116 is presented along line 132 to a Photographic Record readout 134 and through lines 132 and 136 to a Persistent Display Scope 138 which may be utilized for purposes of patient positioning and other information desired by the operator. Similarly, the y-axis spatial channel information derived from Gated Integrator function 126 is presented along line 140 to Photographic Record output 134 and through lines 140 and 142 to Persistent Display Scope readout 138. Readout control to Photographic Record 134 and Persistent Display Scope function 138 is derived from Gate Control and Display Control function 108 through lines 144 and 146. The control asserted thereby is one wherein outputs 134 and 138 are not actuated or are blanked until control function 108 receives an input display signal from Pulse Height Analysis function 104 through line 148. Interrogation of function 104 is provided from control 108 through line 150. In accordance with the invention, inasmuch as a relatively extended time constant, $\tau_e$, is utilized at Summing function 102, any pulse pile-up phenomena will be integrated to derive a peak pulse level beyond the window limitations of the signal channel analyzer operating within function 104. Accordingly, error otherwise introduced into the system from the spatial channel is blanked upon the assertion of an interrogation request from line 150 and a responding blanking type signal or no response signal from function 104 through line 148.

Figure 6:
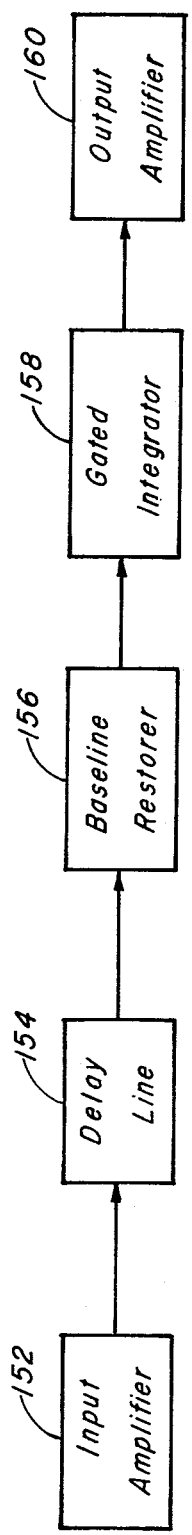
FIG. 6 is a schematic block diagram of a gated integrator configuration which may be utilized with the instant invention.

Looking now to FIG. 6, a block schematic diagram is provided showing the basic components of the Gated Integrator and associated functions depicted generally at blocks 116 and 126 in FIG. 5. Note that the circuit includes an input amplifier 152 which feeds, in turn, into a delay line 154. Delay line 154 is utilized to insure that the integrator gates are open before any spatial informational pulse arrives thereat. The circuit further includes a base line restorer, as at 156, which operates in cooperation with gated integrator 158. The output of integrator 158 is directed to an output amplifier 160, the output from which is directed along lines 132 or 140, as shown in FIG. 5, depending upon the particular orthogonal sense of the incoming signal. A corresponding and more detailed schematic representation of the circuit is revealed in FIG. 7. Referring to that figure, either of the coordinates' spatial inputs as developed at lines 124 or 114 (FIG. 5) is asserted through an input resistor 162 to an amplification stage 164. Stage 164, corresponding to amplifier block 152 in FIG. 6, includes a feedback line incorporating feedback resistor 166, as well as a ground reference input at line 168. Delay line 154 is shown represented at 170 receiving an input from output 172 of amplifier 164. A resistor 174 is coupled between delay line 170 and ground, while the output thereof is AC coupled through capacitor 176 to the input of a base line restorer function. The base line restorer is of a Robinson type as is generally described, for instance, in the following publication:

XVII. Robinson, L. B., "Relation of Baseline Shift in Pulse Amplitude Measurements", Rev. Sci. Inst., 32, 1961, p. 1057.

Essentially, the restorer function is provided for the purpose of assuring a net zero charge value at the gated integrator input prior to the reception of any input signal. Further, the restorer defines the maximum charge that can be placed on the coupling capacitor 176. In the absence of the restoring function, the gated integrator would integrate areas below the baseline as well as under the Gaussian shaped spatial signal. For carrying out its assigned functions, the restorer includes an emitter-follower stage at NPN transistor 178, the base of which is coupled through resistor 180 and line 182 to one side of capacitor 176. The emitter of transistor 178 is coupled through a resistor 184 to $-V_{cc}$ potential, while its collector is coupled through a resistor 186 to $+V_{cc}$. The restorer function additionally includes a current supply network operating such that, upon the occurrence of spurious elevations of current, accommodation is made to control the quiescent point at the emitter-follower stage 178. Note that this current supply includes a PNP transistor 188, the emitter and base of which, respectively, are coupled through resistors 190 and 192 to $+V_{cc}$. This base, additionally, is coupled to ground through a resistor 194. The collector of transistor 188 is coupled through diode 196 to line 182 and through diodes 198 and 200 to a variable resistor 202, the termini of which are connected between the positive and negative sides of the supply voltage.

The output of the base line restorer function is coupled through resistor 204 to one terminal, for instance the source, of a field effect transistor (FET) 206 representing the input of the gated integrator function, while the opposite electrode of the transistor is coupled to line 208. Line 208, in turn, is directed to one side of an integrating amplifier 210. The gate input to FET 206 is present at line 212 and is shown as selectively receiving a signal designated $\overline{\gamma}$ from the control function 108 (FIG. 5). Also influencing line 208 is a network including line 214 and variable capacitor 216 which is coupled to receive an input designated $\gamma$. The opposite input to amplification stage 210 is coupled to ground through line 218. Amplification stage 210 performs an integrating function by virtue of its feedback connection with an integrating capacitor 220 coupled between lines 222 and 224. A shunting resistor 226 is coupled between lines 222 and 224 in parallel with capacitor 220 and is selectively activated by a reset gate present as field effect transistor (FET) 228, the source and drain terminals of which are connected in switch defining fashion within line 224 and the gate input to which at line 230 is configured to selectively receive a reset signal identified as $\overline{\beta}$ from Gate Control function 108 (FIG. 5). A variable resistor 232 is connected between the positive supply voltage and the interconnection of resistor 226 with FET 228. The output of amplification stage 210 is present at line 234 and is coupled through a variable capacitor 236 and line input 238 for selectively receiving a signal input identified as $\beta$.

The output at line 234 of the gated integrator is directed through resistor 240 to the input of a unity gain inverting amplifier 242 which includes a feedback line incorporating resistor 244 and is connected with ground reference at line 246. The output of the amplifier, at line 248, is that represented in FIG. 5 either at line 132 or line 140 and is directed to the readout components of the camera system. As will be apparent in the discussion to follow, gate control over integrator 158 is derived by the noted signal inputs into lines 212, 214 and 230 and 238.

Figure 8:
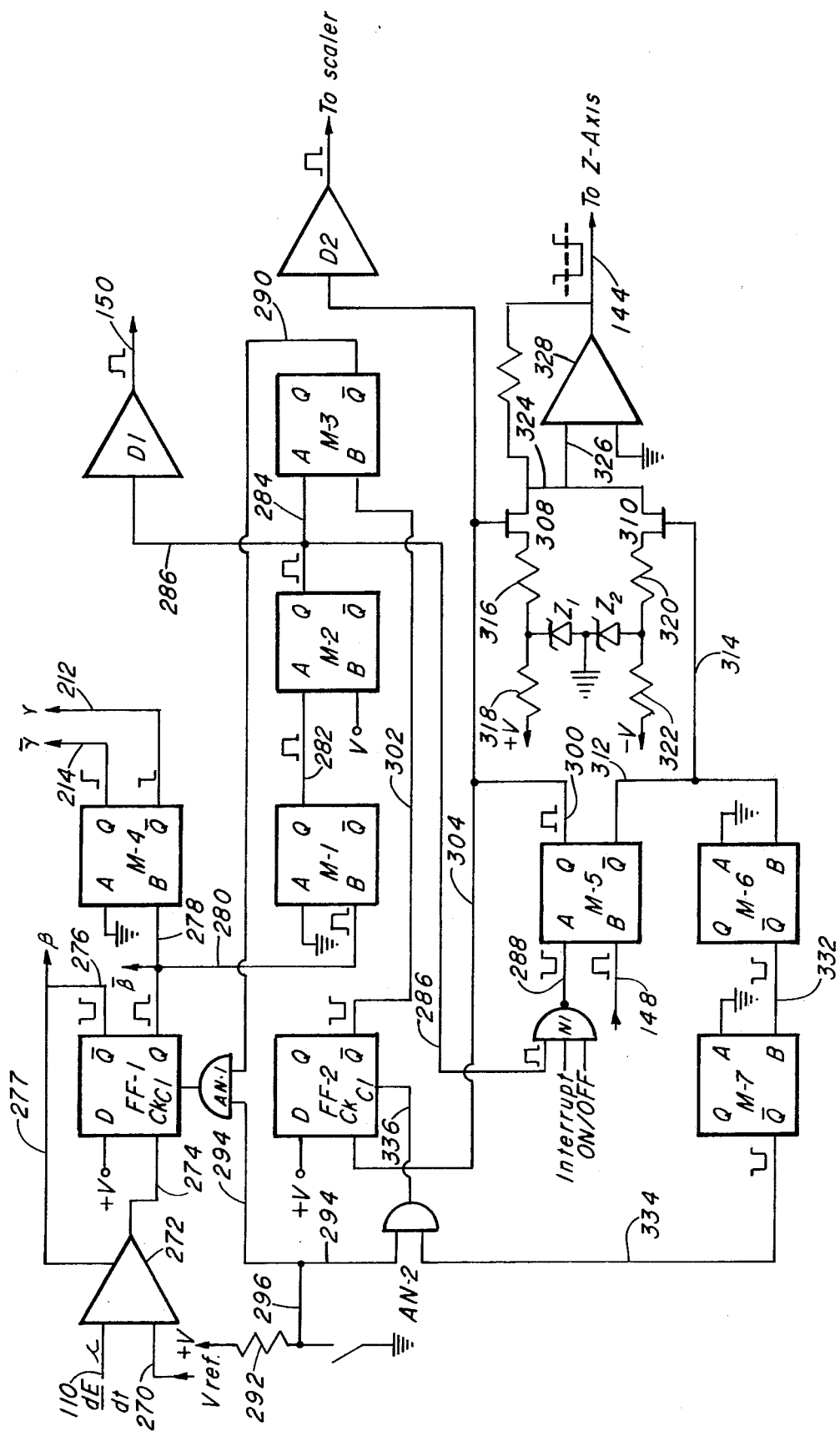
FIG. 8 is a schematic representation of the logic components of a control arrangement according to the invention.
Figure 9:
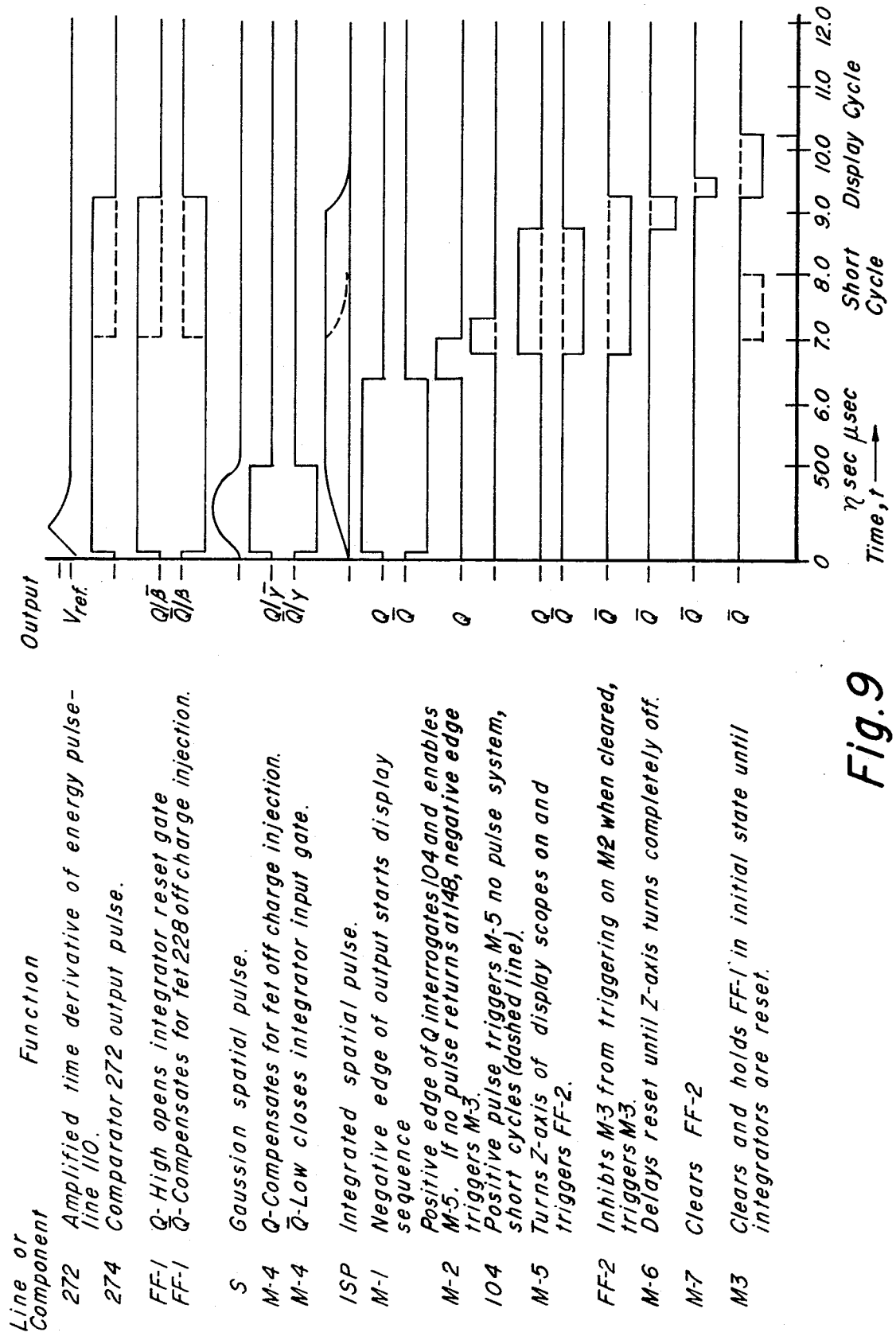
FIG. 9 is a circuit timing diagram corresponding with the schematic representation shown in FIG. 8.

Looking to FIGS. 8 and 9, the control circuit represented in FIG. 5 at 108 is disclosed in more detail in combination with a timing sequence diagram. At time, $t = 0$, as shown in the timing diagram of FIG. 9, the system is prepared to process an incoming set of signals or pulses. The time derivative of the energy pulse or signal $dE/dt$ is directed along line 110 to a comparator 272. When its value exceeds a reference voltage representing the lower level of the window level established by evaluation of Pulse Height Analysis function 104 (FIG. 5) it serves as a start or to actuate the control system. The voltage reference against which the derivative of the energy pulse or signal is compared is inserted from line 270 to the comparator. These predetermined, preliminary signal level conditions being met, comparator 272 provides a positive going output pulse at line 274 which is introduced to a dual, D-type flip-flop FF-1. Conventionally, the D form of flip-flop in corporates an actuating (clock) input signal terminal, Ck, along with a signal input terminal, D. The flip-flop output signal Q becomes 1 at the time of a 0-to-1 change at the clock terminal. In conventional manner, the Q output of the flip-flop represents the inverse of the $\overline{Q}$ output. The D flip-flop also is characterized in incorporating a clear feature designated at "C1" in the diagram. To further facilitate the description of the circuit, Boolean designation is utilized to represent input or output values. For instance, a "low" signal is considered to be one having a potential essentially at ground and is typically represented by a logical "zero". Conversely, a "high" signal is considered positive and may be depicted by a logical "one".

Figure 7:
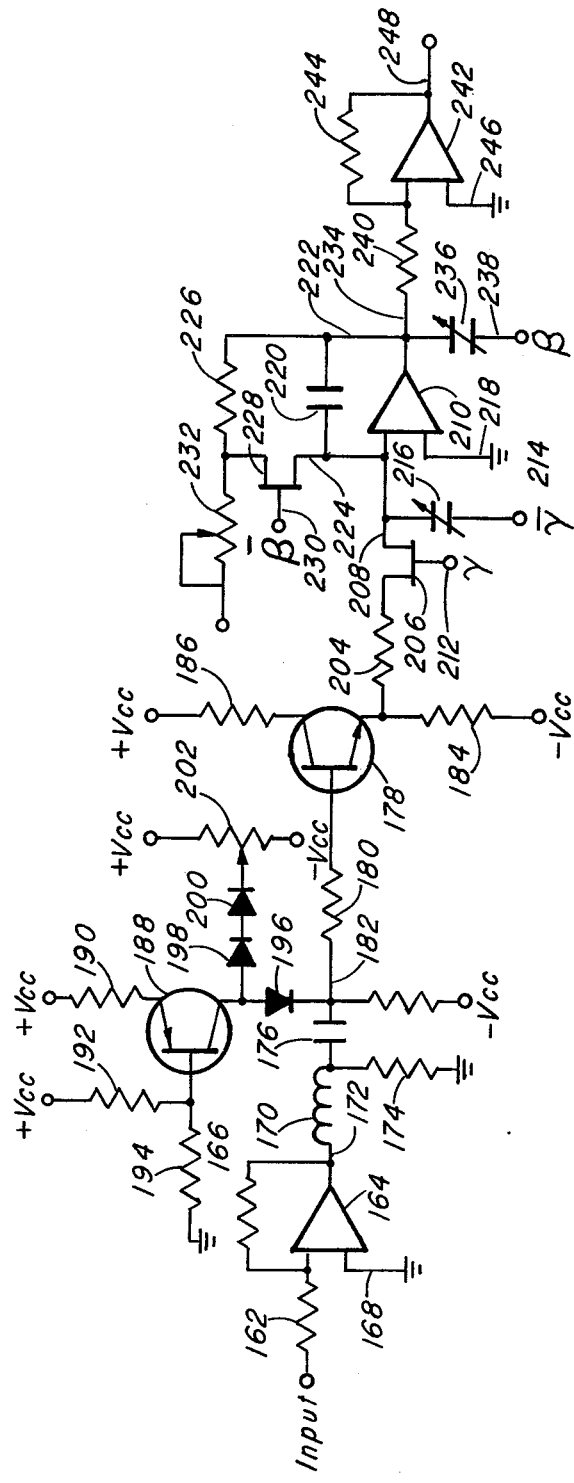
FIG. 7 is a schematic circuit representation of the configuration described in connection with FIG. 6.

Returning to FIGS. 8 and 9, with the presence of a positive going pulse at line 274, flip-flop FF-1 is clocked such that its Q output at line 278 assumes a high value and its $\overline{Q}$ output at line 276 assumes a low value. Note that the Q output of flip-flop FF-1 is identified as $\overline{\beta}$ and is introduced to the reset gate of each integrator, as shown in FIGS. 5-7. With the opening, for instance, of reset gate transistor FET 230, the shunt about timing capacitor 220 is removed to enable the integrating amplifier. Similarly, the $\overline{Q}$ output of flip-flop FF-1 assumes a low status and, by connection through line 276, couples the $\beta$ signal input to the gated integrator as at line 238 in FIG. 7. This $\beta$ signal output of the flip-flop FF-1 is used to compensate for charge injection into the feedback capacitor caused by the capacitance coupling between the gate and drain electrodes of FET 228.

The Q output of flip-flop FF-1 additionally is presented through line 278 to the B input terminal of a monostable multivibrator M-4, and, through line 280, to the B input terminal of monostable multivibrator M-1. Accordingly, these multivibrators are triggered, the $\overline{Q}$ output of multivibrator M-4 being programmed for closing each integrator input gate for a time slightly greater than the base width of the Gaussian shaped spatial pulses. In this regard, note that the $\overline{Q}$ output, as is represented at line 212 of the multivibrator M-4, carries a $\overline{\gamma}$ signal which is introduced into the output gate of FET 206 (FIG. 7). Simultaneously, an inverted $\overline{\gamma}$ input is provided along line 214 to variable capacitor 216 to provide compensation for off charge injection. The gated integrator then commences an integrating mode of performance, the time over which operation is controlled by multivibrator M-4. It may be observed that multivibrator M-4 retains this output state in correspondence with a spatial time constant determined interval, $t_s$, as is more clearly portrayed in FIG. 9. Note in that figure, the representation of a Gaussian spatial pulse, S, corresponding with the activation of the integrator function.

As noted above, the Q output of flip-flop FF-1 also is introduced to the B input terminal of monstable multivibrator M-1. With the presence of the forward edge of this signal at line 280, the Q output of the latter alters from a low to a high value and retains such value over an interval, $t_e$, selected for delaying the start of the display sequence until the energy pulse has been analyzed at pulse height analysis function 104 as shown in FIG. 5. Note that this interval, $t_e$, always will be greater than the integrating interval, $t_s$. The Q output of multivibrator M-1 is coupled through line 282 to the A input of monostable multivibrator M-2. On the occurrence of the negative edge of the pulse of the Q output of multivibrator M-1, multivibrator M-2 is triggered and the resultant Q output transition thereof is directed along lines 284 and 286 to driver circuit D1. The output at line 150 of driver D1 serves as the earlier described interrogation pulse directed to the pulse height analysis function 104 described in connection with FIG. 5. Note additionally, that line 286 extends to one input of a NAND gate N1. Accordingly, the signal from line 286 is inverted and introduced through line 288 to the A input terminal of monostable multivibrator M-5. This input serves to enable the latter to permit the carrying out of a full control cycle. During typical display operation of the camera system, the "interrupted" and "on/-off" inputs to NAND gate N-1 are high at the option of the operator. By converting either or both to a low value, multivibrator M-5 is inhibited to, in turn, inhibit the displays as referred to earlier in FIG. 5 at 134 and 138.

The remaining components of the circuit function on the basis of whether an interrogating signal issued from line 150 to Pulse Height Analysis function 104 (FIG. 5) has been responded to, along line 148, to indicate a pass or no pass condition of signal energy level. If function 104 does not respond to the interrogating pulse from line 150, thus indicating that the peak value of the energy pulse did not fall within the window setting of the evaluation function, multivibrator M-5 receives no signal input at terminal B thereof. Additionally, upon the occurrence of the negative edge of the Q output signal of multivibrator M-2, multivibrator M-3 is triggered from line 284 such that its Q output at line 290 asserts a clearing signal through AND gate AN1 to the clear input terminal, C1, of flip-flop FF-1. The output thereof, as reflected at the multivibrator M-4, causes the integrator to be reset. With this operation, the system is short cycled, and the through-put rate thereof advantageously is increased. Note, that the opposite input at line 294 of AND gate AN1 is normally high by virtue of its connection through line 296 and resistor 292 to a positive voltage source.

Assuming that multivibrator M-5 has been enabled from the line 288, A, input thereto and that a positive response has been received from Pulse Height Analysis function 104 and line 148 at the B terminal input thereto, the multivibrator will react by developing a positive output pulse at its Q terminal and line 300, while a pulse of opposite sense is developed at its $\overline{Q}$ output along line 312. The Q output signal at line 300 is directed to line 304 whereupon it addresses the clock input, Ck, of D flip-flop FF-2. In consequence, the $\overline{Q}$ output of flip-flop FF-2, at line 302, converts to a low value which is asserted at the B input of multivibrator M-3 to inhibit the output thereof. The short cycle feature thereby is inhibited. This signal at line 304 may also be utilized for clocking a scaler or count recording apparatus through a driver circuit D2.

The outputs of multivibrator M-5 also are utilized to switch a Z-axis driving circuit from a negative to positive voltage, thereby turning on the display functions represented in FIG. 5 at 134 and 138. In this regard, note that line 304, carrying the Q output of multivibrator M-5, is connected to the gate electrode of a field effect transistor (FET) 308. By corresponding connection, the $\overline{Q}$ output of multivibrator M-5 is asserted along lines 312 and 314 to the gate input of field effect transistor (FET) 310. Note that the drain-to-source channel of FET 308 is connected through resistors 316 and 318 to a positive voltage source, while the corresponding source-to-drain channels of FET 310 are coupled through resistors 320 and 322 to a negative voltage supply. The respective opposite sides of FET's 308 and 310 are connected through line 324 and line 326 to one input of a Z-Axis amplifier 328 and are biased such that, under conditions wherein monostable multivibrator M-5 is not clocked, the output of amplifier 328 is retained at a negative value. Upon the clocking of multivibrator M-5, however, FET 310, in effect, closes while FET 308 opens, to cause the output of amplifier 328 to change from a negative to positive value, thereby permitting the activation of display and record functions 134 and 134 (FIG. 5).

Zener diodes as at $Z_1$ and $Z_2$ are present in the input network to Z-axis amplifier 328 for the conventional purpose of voltage regulation, the diodes being commonly coupled to ground at their respective anodes. Additionally, the respective cathodes of the diodes $Z_1$ and $Z_2$ are coupled at the common connections of resistors 316 and 318, 320 and 322.

Looking further to the outputs of multivibrator M-5 as they respond to an energy evaluation input at line 148, the positive edge of the output signal at $\overline{Q}$ thereof also activates a multivibrator M-6 in consequence of the connection of line 312 with the B terminal thereof. Multivibrator M-6 serves to provide a delay function assuring an adequate interval for turning off the electron beams of display scopes and the like. The $\overline{Q}$ output of multivibrator M-6 is coupled through line 332 to the B terminal input of another monostable multivibrator M-7. The positive going edge of the $\overline{Q}$ output signal of multivibrator M-6 triggers multivibrator M-7 to provide a corresponding pulse signal at its $\overline{Q}$ output at line 334. Line 334 is coupled through AND gate AN2, the output of which is coupled through line 336 to the clear terminal, C1, of flip-flop FF-2. The opposite input to AND gate AN-2 is operator preselected and is asserted from line 294. With the presence of a clearing input to flip-flop FF-2, the $\overline{Q}$ output thereof at line 302 returns to a high status which, in turn, is imposed at the B input of multivibrator M-3 which, in turn, functions to clear flip-flop FF-1 by virtue of the connection therewith of its $\overline{Q}$ output at line 290 through AND gate AN-1. With the clearing of flip-flop FF-1, the gated integrator is discharged or reset through the $\overline{\beta}$ input signal at line 230, described earlier in connection with FIG. 7.

With the noted return of monostable multivibrator M-3 to its standby state, the control system is fully reset and ready to process another set of information signals. If the output of comparator 272 is high at this time, the system will not process such incoming information. This lock-out feature prevents the partial integration of spatial pulses too narrowly spaced in insertion time. Note that comparator 272 is coupled to receive the $\beta$ signal output from the Q terminal of flip-flop FF-1 through lines 276 and 277. This input signal is utilized by the comparator as a block to any enabling of the system to respond to incoming signals until such time as a full cycle of evaluation has terminated. FIG. 9 reveals the time-based corresponding between the output of comparator 272 and the $\overline{Q}$ output or $\beta$ signal of flip-flop FF-1. In the absence of such $\beta$ signal input from line 277, error would be introduced into the system, for instance, by virtue of the generation of start signals at line 274, integrator timing is disrupted to invalidate an ongoing signal processing procedure. As may be evidenced from FIG. 9, the $\beta$ signal input from line 277 (flip-flop FF-1, $\overline{Q}$ terminal) serves to inhibit comparator 272 until the reset point of a given signal processing cycle.

As noted earlier, any display of spatial pulses which overlap is prevented because, for the optimized filtering system, the base width of the spatial Gaussian pulse is less than the peaking time of the energy Gaussian pulse or interval of energy analysis. Because of this, should two or more gamma arrays photoelectrically interact with the detector and their total energy be absorbed in a time less than the rise-time of the filtered energy pulse, the resulting energy pulse peak value would not fall within the window defined at pulse height analysis function 104. As a consequence, the control system would carry out a short cycle function as revealed in the timing diagram of FIG. 9 by a dashed line alteration of the curves.

Examination of the dashed curves of FIG. 9 reveals that, upon interrogation of Pulse Height Analysis 104, should no response signal be received therefrom within the interrogation interval defined by multivibrator M-2, the negative going edge of the output thereof causes multivibrator M-3 to carry out a reset function, thereby inhibiting the carrying out of the remainder of the signal processing cycle.

Since certain changes may be made in the above system and apparatus without departing from the scope of the invention herein involved, it is intended that all matter contained in the above description or shown in the accompanying drawings shall be interpreted as illustrative and not in a limiting sense.

We claim:

1. In a system for imaging the distribution of a radiation emitting isotope within a region of interest, said system including solid state strip array type detector means having strip regions which are operatively associated with impedance networks, said networks being arranged to receive radiation-induced charges in spatial disposition corresponding with the interaction location of said radiation upon said strips, said charge receipt being time variant in correspondence with said position of interaction to exhibit a collection time constant, $\tau_D$, the improvement comprising:

amplifier means coupled with said impedance network means and having output signals corresponding with said charge receipt;

first summing means responsive to said amplifier means output signals for deriving a spatial signal corresponding to the spatial orientation of a said interaction location;

second summing means responsive to said amplifier means output signals for deriving an energy signal of value corresponding with the spatial signal;

evaluating means responsive to said second summing means energy signal for evaluating the peak value of said energy signal over a time, $t_e$, and having a select output when said energy signal peak value lies within predetermined limits;

means for intergrating said spatial signal over a time, $t_s$, to derive an integrated spatial signal, said time, $t_e$, being greater than said time $t_s$;

readout means responsive, when actuated, to receive said integrated spatial signal and derive perceptible information corresponding thereto; and control means for regulating an operational cycle of said system including the actuation of said readout means only upon the occurrence of said evaluating means select output.

2. The improved imaging system of claim 1 in which:

said first summing means is configured for subtractively summing the said output signals of said amplifier means to derive said spatial signals; and said integrating time, $t_s$, is selected as about equal to or greater than one-eighth the said collection time constant, $\tau_D$, of said solid state detector means.

3. The improved imaging system of claim 1 in which said first summing means includes means effecting a Gaussian pulse shaping of said amplifier means output signals; and said integrating time, $t_s$, is selected as about equal to or greater than one-eighth the said collection time constant, $\tau_D$, of said solid state detector means.

4. The improved imaging system of claim 1 in which:

said first summing means is configured for subtractively summing the said output signals of said amplifier means and for effecting a Gaussian pulse shaping of said subtractively summed signals to derive said spatial signals as Gaussian shaped pulses; and said integrating time, $t_s$, is selected as about equal to or greater than one-eight the said collection time constant, $\tau_D$, of said solid state detector means.

5. The improved imaging system of claim 1, wherein:

said second summing means is configured to additively sum the said amplifier means output signals associated with a said impedance network and includes a high-pass filtering stage means deriving a time derivative signal of said summed output signals; and including comparator means responsive to the value of each said summing means derivative signal equaling or exceeding a predetermined reference value for deriving a start output; and said control means is operative in response to said start output.

6. The improved system of claim 1 in which said control means is configured and arranged to terminate a said operational cycle in the absence of said evaluating means select output subsequent to said time, $t_e$.

7. The improved system of claim 1, wherein:

said second summing means is configured to additively sum the said amplifier means output signals associated with a said impedance network, and includes a stage deriving a time derivative signal of said summed output signals;

said system includes comparator means responsive to the value of each said summing means derivative signal equaling or exceeding a predetermined reference value for deriving a start output; and said control means is operative to effect the commencement of a said operational cycle in response to said start output, and is further configured for terminating said operational cycle in the absence of said select output within a select interval following said time, $t_e$.

8. The improved imaging system of claim 7, in which:

said first summing means is configured for subtractively summing the said output signals of said amplifier means to derive said spatial signals; and said integrating time, $t_s$, is selected as about equal to or greater than one-eighth the said collection time constant, $\tau_D$, of said solid state detector means.

9. The improved imaging system of claim 7, in which:

said first summing means includes means effecting a Gaussian pulse shaping of said amplifier means output signals; and said integrating time, $t_s$, is selected as about equal to or greater than one-eight the said collection time constant, $\tau_D$, of said solid state detector means.

10. The improved system of claim 7, in which:
said control means is configured for interrogating said evaluating means for the presence or absence of said select output at the termination of said time, $t_e$, and for responding thereafter to the presence of said evaluating means select output to actuate said readout means.

11. The improved system of claim 1, in which:
said integrator means is configured for actuation by gating at the commencement and termination of said time, $t_s$, to provide a trapezoidal-type filtering function;
said second summing means is configured to additively sum the said amplifier means output signals associated with a said impedance network and includes a stage deriving a time derivative signal of said summed output signals;
said system includes comparator means responsive to the value of each said summing means derivative signal equaling or exceeding a predetermined reference value for deriving a start output; and
said control means is configured for gating said integrator means to commence said time, $t_s$, in response to said start output.

12. The improved imaging system of claim 11, in which:
said first summing means is configured for subtractively summing the said output signals of said amplifier means to derive said spatial signals; and
said integrating time, $t_s$, is selected as about equal to or greater than one-eighth the said collection time constant, $\tau_D$, of said solid state detector means.

13. In a system for imaging the distribution within a region of interest of a radiation-emitting isotope, said system including solid state detector means having charge characterized outputs representative of the energy and spatial disposition of corresponding interactions of said radiation with said detector means, the improvement comprising:
amplifier means responsive to said detector means outputs and having output signals corresponding thereto;
first summing means responsive to said amplifier means output signals for deriving spatial signals in correspondence with spatial orientations of said interactions;
second summing means responsive to said amplifier means output signals for deriving energy signals of value corresponding with the energy values of said first summing means spatial signals, said second summing means including a stage deriving the time derivatives of said energy values of said amplifier output signals;
evaluating means responsive to said second summing means energy signals for evaluating the peak value of substantially each said energy signal over a time, $t_e$, and having a select output when said energy signal peak value lies within predetermined limits;
means actuable to treat said spatial signals to improve the signal-to-noise aspects of said system;
readout means responsive, when actuated, to receive said treated spatial signals and derive output information representative thereof;
comparator means responsive to the value of each said second summing means derivative signal equaling or exceeding a predetermined reference value for deriving a start output; and
control means responsive to said comparator means start output for actuating said means treating said spatial signal, so as to effect the commencement of an operational cycle of said system.

14. The improved system of claim 13 in which said control means is operative to terminate said operational cycle in the absence of said evaluating means select output following said time, $t_e$.

15. The improved system of claim 13 in which said control means is operative to actuate said readout means upon the occurrence of said evaluating means select output.

16. The improved system of claim 13 in which:
said control means is configured to terminate said operational cycle in the absence of said evaluating means select output following said time, $t_e$; and is further configured and arranged to actuate said readout means upon the occurrence of said evaluating means select output.

17. The improved system of claim 13, in which said control means is configured for interrogating said evaluating means for the presence or absence of said select output at the termination of said time, $t_e$, and for responding thereafter to the presence of said evaluating means select output to actuate said readout means.

18. The improved system of claim 13 in which said control means is operative to remove the said actuation of said spatial signal treating means, following said time, $t_e$, and in the absence of a said evaluating means select output, thereby effecting a short cycle termination of said operational cycle.

19. The improved system of claim 18 in which said time, $t_e$, is selected as that interval, commencing with said evaluating means receipt of a said energy signal, as is required for said energy signal to at least achieve a said peak value lying within said predetermined limits.

20. The improved system of claim 13 in which:
said means for treating said spatial signals comprises integrator means actuable by gating at the commencement and termination of said time, $t_s$, to provide a trapezoidal-type filtering function;
said control means includes logic stage means responsive to said comparator means start output to convert from a first logic condition to a second logic condition for gating said integrator means at said commencement of said time, $t_s$; and
said comparator means is configured and arranged to remain non-responsive to successive inputs thereto to said second summing means input signals in the presence of said control means logic stage means second logic condition, so as to preclude interference to said system on the part of successive said output signals.

21. The improved system of claim 20, wherein:
said integrator means is gatable from a reset condition in response to said comparator means second logic condition; and
said control means logic stage means is configured to assume said first logic condition in the absence of said evaluating means select output following said time, $t_e$, so as to gate said integrator means to said reset condition.

22. The improved system of claim 13, wherein:
the interval of said time, $t_s$, is selected as about equal to or greater than one-eighth the time constant, $\tau_D$, of said solid state detector means; and said interval of time $t_e$, is greater than said interval of time, $t_s$.

23. The improved system of claim 13, in which:

said means for treating said spatial signals comprises integrator means connected to receive said spatial signals and actuable by gating from a reset condition, and subsequently, to a reset condition to carry out trapezoidal filtering of said signals; and said control means includes a logic stage means responsive to said comparator means start output to convert from a first logic condition to a second logic condition for effecting the said gating of said integrator means at the commencement of said time, $t_s$, said logic stage means assuming said first logic condition to effect gating of said integrator means to reassume said reset condition in the absence of said evaluating means select output following said time, $t_e$.

24. The improved system of claim 23 in which said control means is configured to actuate said readout means upon the occurrence of said evaluating means select output.

25. In gamma camera apparatus suited for imaging the distribution of a radiation emitting isotope, said system including a germanium solid state detector arrangement configured having orthogonally disposed arrays of axially aligned strip regions, each strip within each said array being associated with a discrete resistor of a charge splitting resistor network, said networks being arranged to receive radiation-induced charges in spatial disposition corresponding with the interaction location of said radiation with respect to said strips and having termini for providing outputs corresponding to said spatial disposition, said detector arrangement and said resistor networks exhibiting a collection time constant, $\tau_D$, the improvement comprising:

preamplification means coupled at the termini of each said resistor network and having output signals corresponding with said charge receipt;

antisymmetric summing means coupled with said preamplification means for subtractively summing said output signals and deriving coordinate Gaussian filtered spatial signals corresponding to the spatial orientation of a said interaction location;

summing means for additively summing said preamplification means output signals to derive energy signals corresponding with said spatial signals, said summing means including a Gaussian filter having a high pass stage deriving, as a signal, the time derivative of said summed output signals;

gated integrator means coupled with said antisymmetric summing means and configured to receive and integrate said spatial signals over an interval, $t_s$, as defined by an initial and subsequent gating thereof, to provide trapezoidal filtering of said spatial signals;

evaluating means responsive to said summing means energy signals for evaluating the peak value thereof over a time interval, $t_e$, and having a select output when said energy peak value lies within predetermined upper and lower limit value, said time, $t_e$, being greater than said time, $t_s$;

readout means responsive, when actuated, to receive said filtered spatial signals and derive output information representative thereof;

comparator means responsive to the voltage value of each said summing means derivative signal equaling or exceeding a predetermined reference value for deriving a start output; and control means for regulating an operational cycle of said system, responsive to said comparator means start output for carrying out said initial gating of said gated integrator means to commence said integration over said interval, $t_s$, and for actuating said readout means upon the occurrence of said evaluating means select output.

26. The improved gamma camera of claim 25, wherein said time, $t_s$, is selected as about equal to or greater than one-eighth the said time constant, $\tau_D$, of said solid state detector arrangement.

27. The improved gamma camera of claim 25 in which said control means is configured and arranged to terminate a said operational cycle in the absence of said evaluating means output subsequent to said time, $t_e$.

28. The improved gamma camera of claim 26, in which said control means is configured and arranged to terminate a said operational cycle in the absence of said evaluating means output subsequent to said time, $t_e$.

29. The improved gamma camera of claim 28, in which said control means is configured for integrating said evaluating means for the presence or absence of said select output at the termination of said time, $t_e$, and for responding thereafter to the presence of said evaluating means select output to actuate said readout means.

* * * * *